(12) United States Patent
Ivansson

(10) Patent No.: US 6,344,036 B1
(45) Date of Patent: *Feb. 5, 2002

(54) MATERIAL LAYER AND METHOD FOR MANUFACTURING SAID LAYER

(75) Inventor: Anders Ivansson, Halmstad (SE)

(73) Assignee: Duni AB, Halmstad (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/155,698

(22) PCT Filed: Apr. 3, 1997

(86) PCT No.: PCT/SE97/00557

§ 371 Date: Oct. 13, 1998

§ 102(e) Date: Oct. 13, 1998

(87) PCT Pub. No.: WO97/36565

PCT Pub. Date: Oct. 9, 1997

(30) Foreign Application Priority Data

Apr. 3, 1996 (SE) ................................................ 9601302

(51) Int. Cl.[7] .............................................. A61F 13/15
(52) U.S. Cl. ............................. 604/385.101; 604/369; 604/378
(58) Field of Search ............................... 604/369, 378, 604/385.101

(56) References Cited

U.S. PATENT DOCUMENTS

| | | | | |
|---|---|---|---|---|
| 4,560,372 A | | 12/1985 | Pieniak | |
| 5,397,316 A | * | 3/1995 | LaVon et al. | 604/369 |
| 5,514,120 A | * | 5/1996 | Johnston et al. | 604/378 |
| 5,728,446 A | * | 3/1998 | Johnston et al. | 428/167 |
| 5,986,167 A | * | 11/1999 | Arteman et al. | 604/380 |
| 6,096,016 A | * | 1/2000 | Tsuji et al. | 604/378 |
| 6,241,714 B1 | * | 5/2001 | Raidel et al. | 604/378 |

FOREIGN PATENT DOCUMENTS

WO          9701995          1/1997

* cited by examiner

Primary Examiner—John G. Weiss
Assistant Examiner—Michael Bogart
(74) Attorney, Agent, or Firm—Ostrolenk, Faber, Gerb & Soffen, LLP

(57) ABSTRACT

The invention relates to a material layer of soft paper polymer fiber or polymer film intended to be used as a separate layer, or in at least one layer to be placed loosely on, or be bonded to one or more material webs for achieving a controlled diffusion capacity of a liquid deposited on at least the material layer, or for achieving a bulkier and thicker material web. The layer (1) has a plurality of slit formations (2) extending over it, which are laterally arranged in optional and mutually spaced relationship, such as to form free, separate strip formations (3), the layer (1) being intended to constitute a separate material layer or be included in a combination of at least one further, differing material layer or web, which, when the slitted layer (1) is drawn apart to a greater or less extent, positionally fixes the layer in different, given, opened-out configurations, depending on its field of use, this operation resulting in different opening widths being obtained for the slit formations (2) in the material layer.

7 Claims, 2 Drawing Sheets

Figure 1:
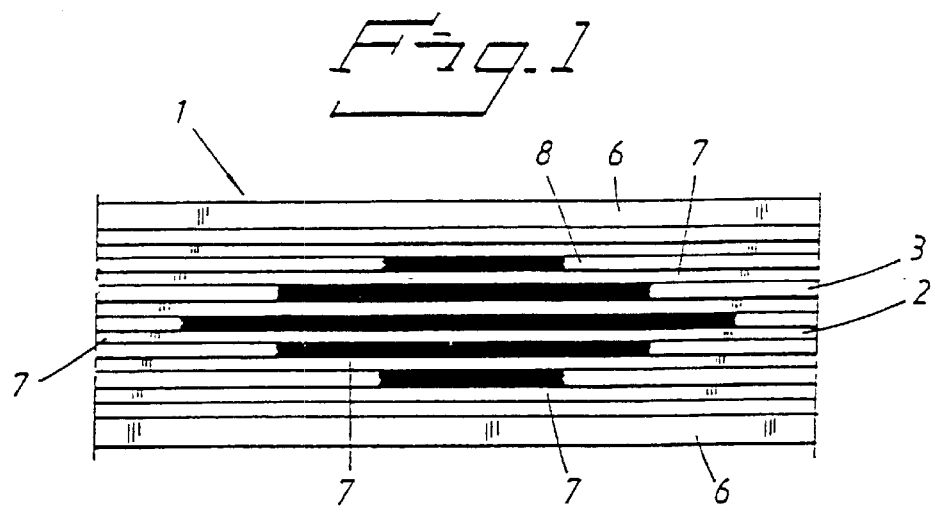

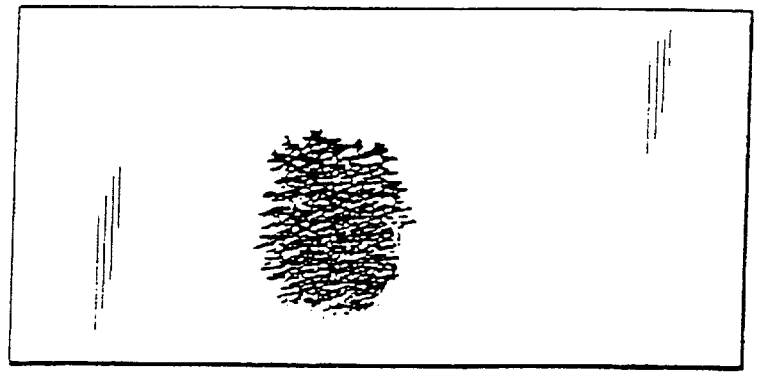
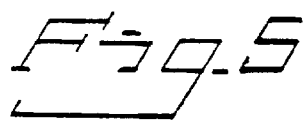
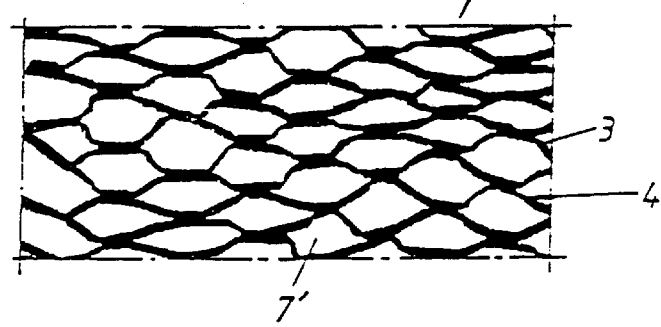
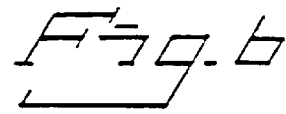
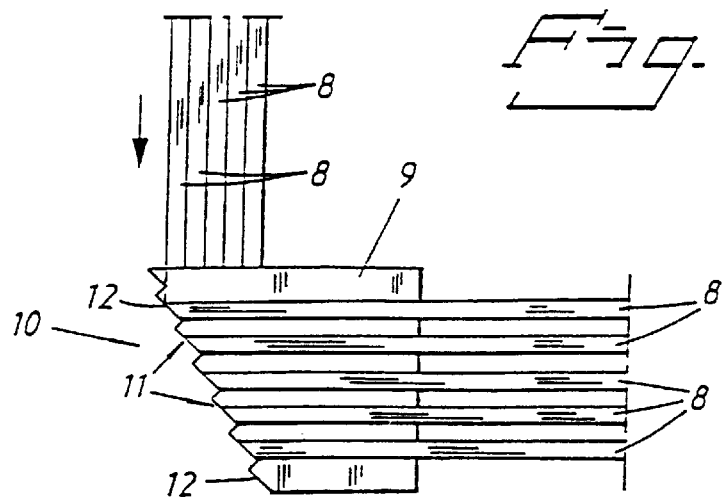

MATERIAL LAYER AND METHOD FOR MANUFACTURING SAID LAYER

The present invention relates to a material layer of either wet- or dry-laid soft paper, including mixtures of polymer and cellulose fibres, fibre fabric or polymer film, the layer being intended for use as a separate layer, or at least in one layer, loosely laid on, or bonded to one or more material layers or webs such as to achieve the controlled diffusion of liquid deposited on at least this separate layer or web, or such as to be a part of a bulkier and thicker material layer or web, the invention also relating to a method of manufacturing the material layer.

A laminate including soft paper in one or more layers is usually the basic material on the market today for table covers, napkins, cleaning rags, face-flannels, bibs, underpant protectors, sanitary towels, absorption products or other table and hygiene products, as well as materials used in the packaging industry. A problem with these known laminates has been that hardly any of them is able to equal, as far as possible, a woven material with characteristics of flexibility and drapability. In addition, the materials used for absorption and in particular such laminates that are used for absorbing body liquids, have limited capacity for controlled diffusion of liquid deposited on them, resulting in that the absorption layer is not optionally utilized.

The object of the present invention is to provide a material layer of the kind mentioned in the introduction, and comprising a quality-determining, flexible material which is able to provide a laminate with a controlled diffusion capacity on the one hand and on the other hand a laminate with bulk.

With the first-mentioned ability of the inventive material layer there is achieved controlled diffusion, at least over the layer, of a liquid deposited thereon, whereby practically optimum utilization of the material absorption capacity may be reached. To this end, the layer is provided with a plurality of slit formations extending over it, laterally in optionally spaced relationship such as to form separate strip formations. These strip formations may be laterally in greater or less spaced relationship, depending on the field of use. In the case where mutual spacing is small and the layer is laminated against a material web with the propensity of being a liquid barrier, effective diffusion of liquid deposited on the layer is effected in the longitudinal direction of the strip formations. This is particularly suitable when the layer is used as a material layer in diapers, sanitary towels or underpant protectors, and with absorption products in general, where controlled diffusion of a liquid deposited on the layer is desirable. The slits may be made with an orientation on the layer according to the functional requirements, i.e. in any attitude from longitudinally to transverse the layer. The slit formations may either be continuous along the entire layer in some suitable direction, or may consist of a plurality of discontinuous slits, between which are formed longitudinal, free-cut strips of the web. If the inventive layer is made up using a less strongly absorbent or diffusive fibre quality, only limited absorption or diffusion takes place in the layer itself, and thus the deposited liquid migrates in the longitudinal direction of the strip formations and in the spaces between the strip formations, while absorption then also occurs on the material webs laminated to the upper or lower faces of the layer.

A method of producing a material layer in accordance with the invention consists of cutting or stamping slits in different patterns in a material, e.g. soft paper, although material having other characteristics and compositions may be used. The slitted layer may be subsequently drawn apart such as to afford different covering percentages of the material surface and to the extent appropriate to the field of use to which the layer is put. It may then be positionally fixed by laminating against one or more adjacent material layers or webs.

In utilizing the other ability of the material layer in accordance with the invention it is placed interiorly in a laminate in combination with other material layers or webs included in the laminate. Since greater bulk is desired here, the layer is drawn apart as in the previous case, causing reticulations to be formed where the slits are, with the strip portions becoming warped as the reticulations are formed. The reticulations may also be filled with foam. The reticulate layer may have a colour differing from the other material webs included in the laminate, and several reticulate layers may be put together in different patterns or be provided with different fillers to obtain such as greater weight, softness, colouring, workability, embossing properties, and absorption capacity. In addition, the laminate containing the inventive reticulate layer can provide a thicker material of a lower weight than would otherwise be possible, and as a result the layer also affords the possibility of liquid being absorbed into the material better. There is also less material needed in the laminate containing the inventive, reticulate layer.

In an alternate embodiment of the invention, the material layer is drawn out so as to be reticulated, causing the strip configurations to become warped, and then cured or "frozen" in this condition with the object of forming a bulky material layer.

Figure 2:
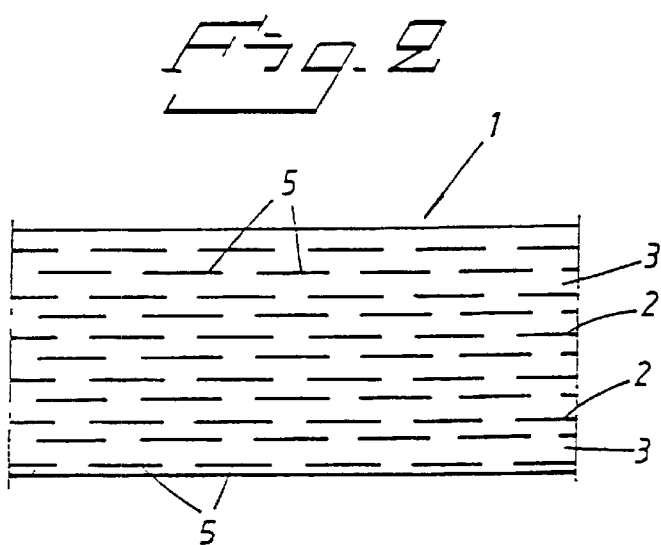
Figure 3:
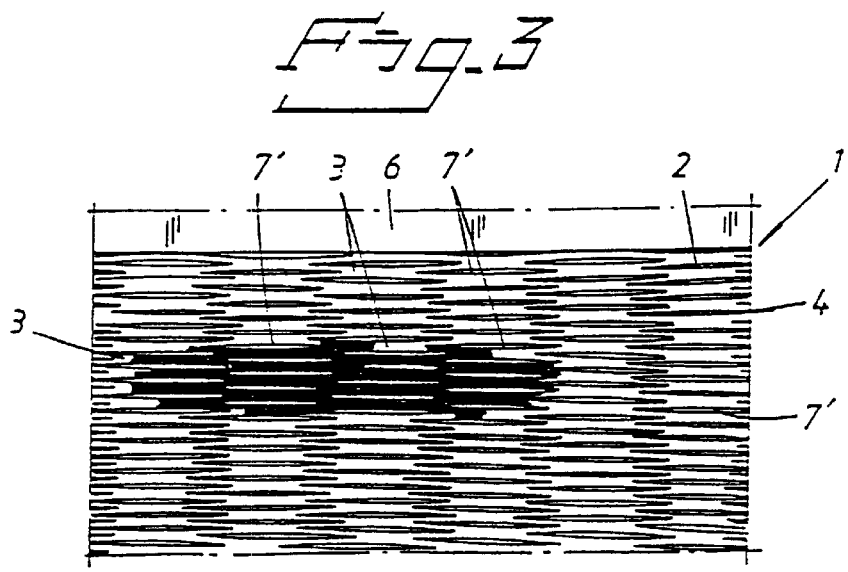

The invention will now be described in more detail below with the aid of some prefered embodiment examples, and with reference to the accompanying drawings, where FIG. 1 illustrates an inventive material layer, which is laminated against a material web in the form of a liquid barrier, with the slit formations in the layer only slightly parted for forming slit openings with completely free-cut strips which effectively propagate the deposited liquid in their longitudinal direction, FIG. 2 illustrates a material layer in accordance with the invention, this layer having a plurality of discontinuous slit formations in the form of slits, situated in line over its surface and in given, mutually spaced relationship and thus forming partial strips, FIG. 3 illustrates the material layer of FIG. 2 after it has been opened out transverse the slits and laminated against a material web in the form of a liquid barrier, such as to obtain controlled migration of liquid in the longitudinal direction of the strips, FIG. 4 illustrates a layer of soft paper, without slit formations and with the same fibre orientation as in FIG. 3, that has been applied to a material web formed as a liquid barrier, a drop of liquid having been deposited on the soft paper layer to demonstrate the diffusion of the liquid in the laminate, FIG. 5 illustrates the layer of FIG. 2 after it has been further opened out such as to form a reticulate layer with warped strip formations, this layer being positionally fixed, with the aid of a bonding agent, between two adjacent material layers, and thus constituting a spacer layer between these two for providing bulkiness, and FIG. 6 illustrates how completely free-cut strips in an inventive material layer are brought into given, mutually spaced relationship before being positionally fixed to an adjacent material web with the aid of deflecting apparatus.

In an embodiment of the invention illustrated in FIG. 2, a material layer 1 is comprised, for example, of soft paper.

This layer is intended to be utilized as a separate layer, or at least in one layer to be placed loosely, or to be bonded against one or more material webs for achieving a bulkier and thicker material web. This is obtained by pulling apart the layer 1, causing the layer to become reticulated as the slit formations 2 open out and the strip formations 3 are warped or twisted to suit, as will be seen from FIG. 5; or the layer may become a laminate for an absorption product according to FIG. 3. The twisted or warped strip formations 3 may, after reticulation, be fixed to two adjacent material webs, the reticulated layer 4 then constituting a spacer providing bulkiness. The reticulated layer 4 is thus intended to be placed between two webs, or against one web, and its reticulations may be filled with different fillers with a foam, to obtain further properties such as greater weight, softness, colouring, workability, embossing characteristics and absorption capacity in the finished laminate.

The laminate containing the reticulate layer 4, with or without foam-filled reticulations, provides a thicker material with lower weight than what would otherwise be the case, and as a result of this the implementation of the layer 4 affords the possibility of rapid absorption of any liquid spillage on the laminate.

The slit formations 2 allowing the formation of reticulations comprise a plurality of slits 5, arranged in lines in mutual spaced relationship both along the lines and laterally. The slits 5 in one line are displaced in relation to the slits 5 in lines on either side, thus enabling special configuration of the layer 1 in response to its field of use. In a preferred embodiment example the strip formations 3 formed by slits 5 may have a width constituting a short, given portion of the length of the slits 5.

In the case where the inventive layer 1 is intended for inclusion in a laminate, where controlled liquid diffusion of a liquid desposited on the layer is desired, e.g. for a baby's diaper or an underpant protector, the slitted layer 1 may be laminated against a material web formed as a liquid barrier 6, with the strip formations 3 only slightly parted to form small slit openings 7 according to FIG. 1, or slit openings 7' according to FIG. 3, whereby a noticeable and effective migration of liquid in the longitudinal direction of the slit and strip formations is achieved when liquid is deposited on the layer. What distinguishes the layer 1 when used in absorbent materials, e.g. diapers or underpant protectors, is that is has a plurality of slit formations 2. These may either be continuous slit openings 7 with completely free-cut strips 8 along the entire layer 1 in some suitable direction, according to FIG. 1, or the slit formations 2 may comprise a plurality of slits 5 arranged one after-the other in lines at small mutual spacing between the strip formations 3, according to FIG. 2. It will be seen from the embodiment example, illustrated in FIG. 3, how a drop of liquid is diffused in the slit material, irrespective of the fibre orientation in the layer 1. In FIG. 4 the layer depicted here has the same fibre orientation as that for the layer in FIG. 3, where a material layer included in the laminate is not slitted in accordance with the invention. It will be noted from this figure that a drop of liquid diffuses mostly transverse the fibre orientation, which particularly applies to soft crepe paper. From FIG. 3, illustrating the same laminate as in FIG. 4, but slitted in accordance with the invention, it will be seen how liquid migrates in the longitudinal direction of the strip formations 3, due to the slits. In addition, by slitting the material web controlled diffusion of liquid deposited on the layer may also be obtained in a direction towards regions of superabsorbent material (SAP) arranged in the laminate. This superabsorbent material (SAP) may then be blended into the fibre material of the layer 1 or disposed in the slit formations 2. The SAP is suitably applied in a pattern consistent with the intended field of use.

The invention also relates to a method of producing a material layer 1, which is intended to be placed in at least one layer, loosely against, or bonded to, one or more material webs for providing a controlled diffusion capacity for a liquid deposited at least on the layer 1, or for providing a bulkier and thicker material web. Distinguishing for the method in accordance with the invention is that the layer 1 is slit to form longitudinal strip formations 3, while the slit formations 2 thus formed extend a given distance from each other, the layer 1 being positionally fixed to at least one material web, after the strip formations 3 have been drawn apart to a greater or less extent.

A deflecting apparatus 9 may be used for drawing apart the completely free-cut strips 8 in accordance with the embodiment illustrated in FIG. 1. As will be seen from FIG. 6, the parallel strips 8 forming the layer 1 are deflected about 90° over the apparatus 9. At its deflecting location 10, which can be an edge 12, the apparatus 9 has a plurality of 45° sections 11 situated one after the other and mutually relatively displaced for guiding and separating the strips 8. At the apparatus 9 the free-cut strips 8 are separated and then positionally fixed in relation to each other, e.g. on a material web in the shape of a liquid barrier 6.

When a part of the inventive layer 1 is included in a diaper or underpant protector as a diffusion layer for liquid deposited on the article, the material from which the layer is produced can be dry- or wet-laid soft paper, or other fibre material possessing capillary properties and which can absorb and permit diffusion, i.e. can have properties of liquid acceptance or gain. The diffusion layer may be single or comprise several layers one upon the other, and they may have different densities for controlling liquid acceptance. In special embodiments, different kinds of SAP may be used in one or more layers and in different concentrations, and of different types to suit desired product properties. The SAP type used is suitably environmentally friendly, biologically decomposeable and made, inter alia, from renewable raw materials.

The web-forming diffusion layer may have a coating, which is either fully covering or perforated and is, for example, a polymer film, dense paper or a liquid product forming a film. When a polymer film is used the slit cuts also result in downwardly bent cut surfaces, which reinforce the diffusion effect, provide reduced rewetting and also a reduced feeling of moistness.

To achieve a "dryness feeling" for the surfaces of the diffusion layer, a coating of permeable material, e.g. nonwoven or such as perforated polymer film, is laminated to the diffusion layer, and this coating drains deposited liquid such as to give a feeling of low moistness in or on the outer material layers.

Different combinations of diffusion layers in accordance with the invention can be envisaged, namely several layers with varied location of any fibre layer with a coating, partially reticulate layers for concentrating absorption, reticulate layers with reticulations of varying sizes for different purposes, diffusion layers with narrow reticulations giving low feeling of moistness, and those with wide reticulations giving rapid liquid acceptance due to their large empty volumes, diffusion layers with reticulations where the slits have optional orientation, e.g. along or transverse web length. Slit length and reticulation width for the diffusion layer may be adjusted to suit requirements, and openings in multilayer products may be in register, or randomly arranged in the Z-direction.

Completely free-cut strips, forming the inventive diffusion layer, may be set on edge in spaced mutual relationship and uncoated, or placed close together if they are coated with film.

In the case where knives are used to make the slits, these knives may be implemented such that they provide rough cut surfaces, which results in greater absorption area, and thus better absorption. Finally, the coating and backing may be vacuum formed to each other with an intermediate, inventive diffusion layer. In some applications it can be advantageous to have an "aspirating" backing.

What is claimed is:

1. Material layer of soft paper or polymer fiber having a plurality of slit formations laterally arranged at an optimal, mutual spacing, defining a number of wholly or partially separated, longitudinally aligned strip formations, wherein, when the material layer is drawn apart, different opening widths are obtained at the slit formations, the slit formations inducing, by capillary action, a controlled diffusion, in the strip formations and in the longitudinal direction of the slit and strip formations, when a liquid is deposited on the material layer.

2. A multi-layer comprising the material layer as claimed in claim 1, wherein the material layer is laminated to a material web in the form of a liquid barrier, said layer having slit formations comprising longitudinal slit openings to form completely free-cut, slightly drawn-apart strips, so that a noticeable diffusion of the deposited liquid is achieved on the layer in the longitudinal direction of the strips.

3. Material layer as claimed in claim 1, wherein the slit formations are longitudinally aligned at a given material spacing in each of a plurality of rows, alternate rows of slits are mutually, longitudinally displaced a given distance in relation to the other rows, and the material layer is expanded transversely of the slits, forming reticulated strip formations.

4. Material layer as claimed in claim 3, wherein when the layer is drawn apart in a direction transverse to the slits, different amounts of warping occur in the strip formations extending between the slits, thereby forming the reticulated strip formations.

5. Material layer as claimed in claim 3, wherein the material layer is laminated to a material web with a bonding agent.

6. Material layer as claimed in claim 5, wherein the reticulated strip formations of the material layer laminated to the material web provide bulkiness.

7. Material layer as claimed in claim 5, wherein the material web is in the form of a liquid barrier.

* * * * *